(12) United States Patent
Millot et al.

(10) Patent No.: US 6,171,289 B1
(45) Date of Patent: Jan. 9, 2001

(54) SAFETY DEVICE FOR COLOSTOMY HAVING A WETNESS DETECTOR AND ALARM

(75) Inventors: Philippe Millot, Orgeux; Laurent Tavernier, Dijon, both of (FR)

(73) Assignee: Plasto SA, Chenove (FR)

( * ) Notice: Under 35 U.S.C. 154(b), the term of this patent shall be extended for 0 days.

(21) Appl. No.: 09/429,042

(22) Filed: Oct. 29, 1999

(30) Foreign Application Priority Data

Nov. 6, 1998 (FR) .................................................. 98 13993

(51) Int. Cl.⁷ .......................................................... A61F 5/44
(52) U.S. Cl. ............................................. 604/336; 344/361
(58) Field of Search ..................................... 604/317, 327, 604/328, 331–332, 336–344, 361

(56) References Cited

U.S. PATENT DOCUMENTS

| 4,356,818 | * | 11/1982 | Macias et al. . |
| 4,796,014 | * | 1/1989 | Chia . |
| 4,865,594 | * | 9/1989 | Thomas . |
| 5,178,615 | * | 1/1993 | Steer et al. . |
| 5,722,965 | * | 3/1998 | Kuczynski . |
| 5,796,345 | | 8/1998 | Leventis et al. . |

FOREIGN PATENT DOCUMENTS

| 2 308 306 | | 6/1997 | (GB) . |
| WO 94/15190 | | 7/1994 | (WO) . |
| WO 95/15739 | | 6/1995 | (WO) . |
| WO96/25904 | * | 8/1996 | (WO) . |

* cited by examiner

*Primary Examiner*—John G. Weiss
*Assistant Examiner*—LoAn H. Thanh
(74) *Attorney, Agent, or Firm*—Evenson, McKeown, Edwards & Lenahan, P.L.L.C.

(57) ABSTRACT

This disposable device for securing an ostomy bag to a stoma created in a patient, of the type comprising means for joining the ostomy bag to an adhesive seal (5) which is applied on the patient via a contact face, a through-passage (8) communicating with the stoma being formed in the adhesive seal (5), of which the contact face on the patient is at least partially covered by an adhesive composition, is characterized in that the adhesive seal (5) additionally comprises means (15, 16, 17, 18, 19) for detecting wetness of the adhesive composition and means for triggering an alarm when a predetermined level of wetness is reached in the adhesive composition.

10 Claims, 2 Drawing Sheets

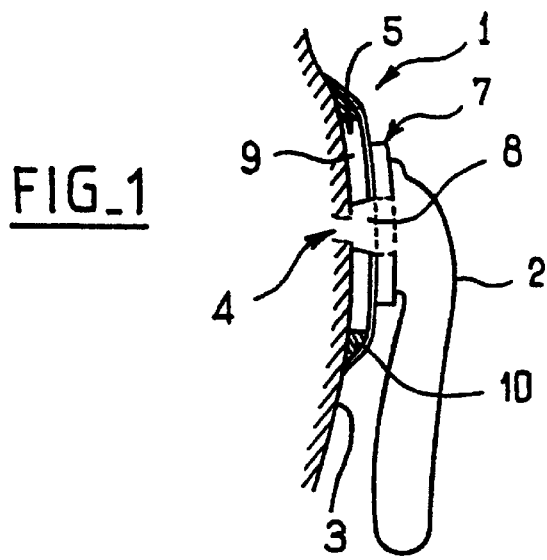
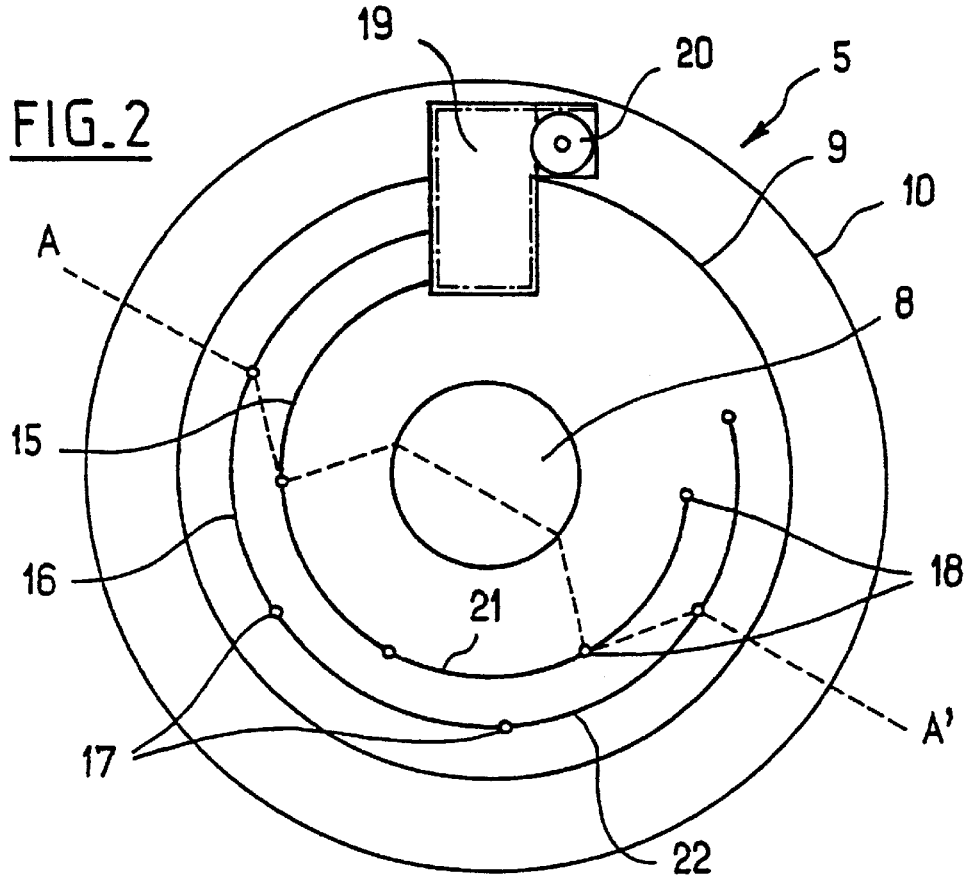
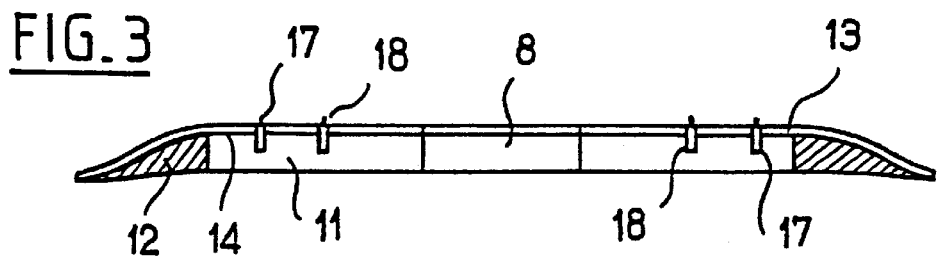

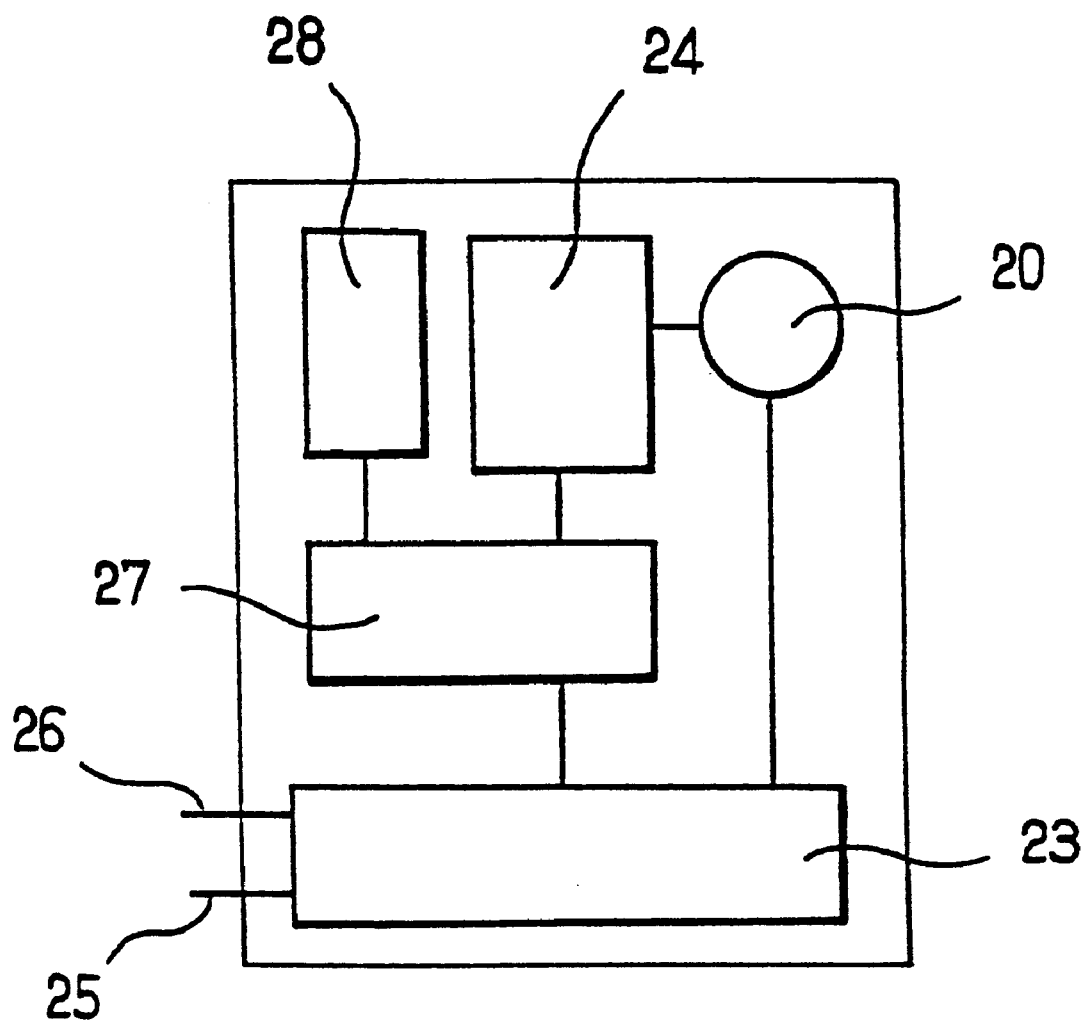

SAFETY DEVICE FOR COLOSTOMY HAVING A WETNESS DETECTOR AND ALARM

The present invention concerns a novel device intended to prevent the risk of inadvertent detachment of an adhesive seal providing for the leaktightness of a colostomy.

PRIOR ART

In certain diseases such as cancer of the colon, it may be necessary to modify the natural course of the intestine and to perform a colostomy, that is to say establish an artificial outlet from the intestine through the abdomen wall, the orifice created being called a stoma and having to be connected to an exchangeable plastic ostomy bag. In practice, the plastic bag must be connected in a leaktight manner to the stoma and, in order to do this, use is made of an adhesive seal which is fixed directly on the patient's skin. This adhesive seal can be directly integral with the bag, which means that the whole assembly must be detached from the skin each time the bag is changed. A system made up of two parts is now more often preferred: a first part comprises the adhesive part to be fixed on the skin, integral with a joining device on which the exchangeable ostomy bag is fixed; this assembly allows the adhesive part to be left in place for several days, which limits the risks of skin irritation caused by repeated removal and fitting of an adhesive. However, there is the problem of knowing at what time it becomes necessary to change the adhesive seal; indeed the adhesive layer of the seal gradually loses its effectiveness until such time as the possible appearance of leaks with unpleasant consequences; it therefore seemed desirable to have a system capable of signalling the need to change the adhesive seal.

It is also known that the adhesive part of the device in direct contact with the skin is preferably an adhesive composition charged with hydrocolloid, the said adhesive composition charged with hydrocolloid being generally well tolerated by the skin in the case of long-term applications. Moreover, as the hydrocolloid is hydrophilic, it gradually absorbs the biological fluids present in the environment, which eliminates one of the causes of the deterioration in the adhesive power of the device as a whole.

Electrical or electronic devices are also known which are capable of detecting wetness in diapers and of signalling the need to change the diaper. For example, EP 810 847 describes an assembly comprising quite a large adjustable electrical circuit and a sensitive strip supporting two electrodes. The sensitive strip is arranged inside the diaper, while the means for processing the signals delivered by the electrodes are arranged in an articulated casing accessible from outside the diaper. After use, the wetness detection strip is removed from the casing and renewed. In order to avoid direct contact between the electrodes and the babies'skin, a permeable layer is applied on the electrodes. However, such a wetness detection device cannot be adapted to a device for securing an ostomy bag, if only because of the difficulty in positioning the detection support strip. Moreover, it is necessary to isolate the electrodes by specific means in order to prevent contact between the electrodes and the babies'skin.

OBJECT OF THE INVENTION

The object of the invention is to propose a technical solution for detecting a risk of leaks from the adhesive of an ostomy bag, the said leak resulting from an appreciable reduction in the adhesive power of the layer of adhesive composition.

SUBJECT OF THE INVENTION

According to the invention, a novel disposable device is proposed for securing an ostomy bag to a stoma created in a patient, of the type comprising means for joining the ostomy bag to an adhesive seal which is applied on the patient via a contact face, a through-passage communicating with the stoma being formed in the said adhesive seal, of which the contact face on the patient is at least partially covered by an adhesive composition containing a hydrocolloid dispersion, and wetness detection means, characterized in that the wetness detection means comprise at least two series of electrodes for measuring conductivity of the adhesive composition, the electrodes being lodged at least in part in the adhesive composition and not being in contact with the patient, and means for triggering an alarm when a predetermined level of wetness is reached in the adhesive composition.

DESCRIPTION OF THE INVENTION

The securing and sealing device according to the invention comprises an adhesive inner face intended to be fixed directly to the patient's skin, around the stoma, and another face provided with a mechanical joining means, able to receive an exchangeable bag.

The adhesive face is in the form of a disc provided, at the centre, with a through-passage, and it can be made up of a single type of adhesive composition containing a hydrocolloid dispersion. It can also be made up of a central disc whose inner face is covered by an adhesive composition of the type described above, surrounded by a peripheral ring whose inner face is covered by an adhesive composition not containing hydrocolloids and having a greater adhesive power than that of the central disc. The adhesive layer (simple or complex) is integral with a flexible support which ensures the connection with the joining means provided for securing the ostomy bag. According to the invention, this flexible support is provided with an electronic circuit capable of measuring the degree of hydration of the adhesive composition charged with hydrocolloids and of activating an alarm means when the degree of hydration of the said adhesive composition becomes greater than a predetermined threshold value, the said threshold value being calculated for a degree of hydration beyond which the adhesive power becomes insufficient to ensure satisfactory securing and sealing of the device.

In practice, a flexible support is used which is non-stretchable and does not conduct electricity, for example a nonwoven of synthetic material. The means for measuring the degree of hydration of the adhesive composition charged with hydrocolloids is composed essentially of two electrodes or electrode lines arranged separately within the thickness of the adhesive composition. These two electrodes are connected to a miniaturized electronic circuit powered by a battery or a cell and capable of measuring the conductivity between the two electrodes. The conductivity of the adhesive composition charged with hydrocolloids increases substantially in proportion to the degree of hydration of these hydrocolloids and, for a given formulation of the adhesive composition and a defined arrangement of the electrodes, it is possible to provide a conductivity value beyond which there is a risk of the adhesive composition no longer ensuring sufficient sealing and adhesion functions because it will have reached an unacceptable degree of wetness.

When this conductivity threshold is reached, the electronic device triggers an alarm means which warns the patient of the need to take action. This alarm means can be connected directly to the device and cause a periodic vibration which the wearer will be able to feel, or activation of a light emitting diode (LED) which the patient will be able to see when checking the device. The alarm means can also be in the form of a radio frequency transmission capable of activating a remote receiver, which can, for example, be combined with a watch which emits a light or acoustic signal.

Other advantages and characteristics will become clearer from reading the description of a preferred embodiment of the invention, and from the attached drawings in which:

FIG. 1 is a side view of the device for securing an ostomy bag;

FIG. 2 is a diagrammatic plan view of an ostomy seal according to the invention;

FIG. 3 is a cross section along AA' in FIG. 2;

FIG. 4 is a synoptic representation of the electronic detection circuit.

The device 1 for securing an ostomy bag 2 on the abdomen wall 3 of a patient, in which a stoma 4 or colostomy has been created, comprises an ostomy seal 5 and means 7 for joining the ostomy bag 2 to the adhesive seal 5.

The ostomy seal 5 is provided, at the centre, with a through-passage 8 which brings the stoma 4 into communication with the ostomy bag 2. The ostomy seal 5, in a preferred embodiment, is composed of a central disc 9 and a peripheral ring 10 surrounding the central disc 9. The inner faces of the central disc 9 and of the peripheral ring 10 are covered, respectively, by an adhesive composition 11 containing hydrocolloids and by an adhesive 12 without any hydrocolloid and having an adhesive power at least equal to and preferably greater than that of the adhesive composition 11. In another embodiment, it is possible to use a flexible support sheet 13 which is non-stretchable and does not conduct electricity, on the inner face 14 of which different adhesive compositions 11 and 12 are placed, such as those mentioned above, the support sheet and the adhesive compositions constituting the ostomy seal 5.

The sheet 13 comprises or supports a printed circuit whose two tracks 15 and 16 are represented in FIG. 2 and each comprise at least one series of electrodes 17, 18. Each track 15, 16 is preferably at least partially concentric with the seal 5, so that the electrodes 17, 18 are distributed on at least an arc of a circle whose centre is coincident with the centre of the through-passage 8. The equipotential track is preferably printed on the outer face of the seal 5 and not covered by adhesive composition and it is connected to a series of micro-electrodes 17, 18 passing through the support sheet and penetrating into the adhesive composition 11 charged with hydrocolloids. Each of the micro-electrodes 17, 18 has substantially the form of a small cylinder of metal and penetrates to about half the thickness of the adhesive composition 11: a good contact is thus ensured between the adhesive composition and the electrode without any risk of contact between the skin and the electrode, which would lead to incorrect conductivity measurements. The two sets of micro-electrodes 17 and 18 are connected to an electronic circuit 19 which is fixed to the outer face of the support sheet 13, and the function of which is to measure the conductivity between the two sets of micro-electrodes 17, 18. The electronic circuit 19 is powered by a cell or a battery 20 and also comprises an alarm means which can be a periodic vibrator or a light emitting diode or a radio emitter capable of activating a receiver which is independent of the device located on the ostomy seal.

The principle of monitoring the effectiveness of the seal according to the invention is based on measuring the conductivity of the layer of adhesive composition 11 charged with hydrocolloids. At the outset, the adhesive composition 11 is charged with non-hydrated hydrocolloids and the conductivity of this adhesive composition, measured between the two sets of micro-electrodes 17, 18, is extremely low; for this reason the electronic system will confirm a substantial resistance. During use, the seal 5 is in contact with the wetness originating either from the material collected in the bag or from transpiration of the patient and the hydrocolloids present in the adhesive composition gradually become charged with wetness on account of their hydrophilic nature. At the same time, the adhesive power of the composition gradually diminishes on account of the swelling of the hydrated hydrocolloids. However, the presence of water and mineral salts accumulated in the hydrocolloids causes an increase in the conductivity of the adhesive composition 11. It will thus be understood that monitoring the conductive power of the adhesive composition 11 makes it possible to provide reliable indications concerning the development of the adhesive power of the seal: by judiciously determining a threshold value for this conductivity, it is possible, without destroying the seal, to establish a limit state in respect of the conductivity, justifying the need to take action because of an appreciable reduction in the adhesive power and because of the risks associated with partial detachment.

In practice, the micro-electrodes 17, 18 are distributed on two concentric circles or arcs of a circle, as is represented in FIG. 2. According to a preferred embodiment, the sensitive parts (micro-electrodes) of the device are distributed only on an arc of a circle, advantageously a half circle 21, 22 which is situated on a sector diametrically opposite the part which supports the integrated circuits responsible for processing the signal. This is because the patients fitted with such devices can generally follow normal activities corresponding to a frequent standing or seated position. For this reason, the lower part of the seal will be much more exposed to wetting than the upper part, and, as a consequence, it suffices to monitor the adhesive power of this lower part of the seal in order to guarantee the greatest risk. This also makes it possible to position the active part of the circuit on the upper half of the seal less exposed to wetness and more accessible. It should be noted that this arrangement can be coordinated with the position of the device for locking the exchangeable bag which is generally placed in the upper part of the seal for the simple reason of accessibility.

The electronic part of the detector is made up of miniaturized elements known to the skilled person for detecting a conductivity threshold and for triggering an alarm means. The circuit diagram of the electronic part is represented in FIG. 4, in which an electrical power source 20 is represented which is generally of the button cell type, the power source powering a current generator 23 and a signalling means 24. The current generator is connected on the one hand to the electrode circuits represented by connections 25 and 26, and, on the other hand, to a voltage comparator 27 which, as a function of the voltage difference between the value measured between the electrode circuits 25 and 26 and a reference value (reference threshold 28), can activate the signalling means 24.

By way of example, it is possible to use an integrated circuit of the MAX951 type from the company Maxim which generates current of the order of 50 $\mu$A, associated with a voltage comparator. When the value of the voltage imposed by the current generator falls to a threshold value, the comparator activates a signalling means.

This signalling means, which can be activated by the comparator, can be, for example, a vibrator, a light emitting diode or a radio frequency emitter of type U2740B from the company Temic, of which the radio signal will be received by an acoustic or light device situated, for example, on a watch on the user's wrist.

In the case of patients who are not independent, the radio signal can activate an alarm situated at the location of the nursing personnel.

By way of example, a device according to the invention has been produced in which the adhesive composition 11 containing sodium carboxymethylcellulose and obtained according to the recommendations of document FR 2753380 (example 1) was deposited by transfer, at a thickness of 1.5 mm, on the inner face 14 of a film 13 of polyvinyl having a thickness of 0.1 mm. This film 13 supports, on its outer face, the electronic circuit and the electrodes as represented in FIG. 2. The electrodes 17, 18 pass through the film 13 and project by about 1 mm on the inner face. For this reason, they penetrate into the layer of adhesive composition by about two thirds of the thickness.

The joining device intended to secure the flexible bag and known per se is then crimped to the whole arrangement in a leaktight manner in order to protect the parts of the film supporting the electrodes. The electronic part comprises an integrated circuit sold by the company Maxim under the reference MAX951, ensuring the functions of current generator and threshold detector, and connected to the two series of electrodes and to a light emitting diode. The whole arrangement is powered by a button cell. The battery is switched on at the time when the seal is extracted from its packaging, by means of withdrawal of a film which insulates a pole of the button cell and which remains integral with the packaging. The monitoring of the degree of wetness of the seal is continuously effective as from the time of withdrawal of the seal from its packaging. When a part of the seal is impregnated with wetness in a sufficient quantity (the alarm means was triggered when the seal had lost about half of its adhesive power on a plate of glass), the light emitting diode (LED) is activated and can remain lit until the patient checks and sees that it is necessary to provide a new seal.

The system described here for a colostomy seal can be used in an analogous manner for any ostomy seal, for example an ileostomy or a ureterostomy.

What is claimed is:

1. A disposable device for securing an ostomy bag to a stoma created in a patient, said device comprising an adhesive seal having an outer face and a contact face, the adhesive seal to be applied to said patient via said contact face, said adhesive seal having a through-passage which communicates with the stoma when in use, said contact face being at least partially covered by an adhesive composition containing a hydrocolloid dispersion, a joining element which joins the ostomy bag to said adhesive seal, a wetness detector comprising at least two series of electrodes for measuring conductivity of the adhesive composition, said electrodes for lodging at least in part in the adhesive composition and not to be in contact with the patient, and a trigger which triggers an alarm when a predetermined level of wetness is reached in the adhesive composition.

2. The disposable device according to claim 1, wherein each series of electrodes is distributed on at least an arc of a circle concentric with the center of the through-passage.

3. The disposable device according to claim 1 or 2, wherein the detector comprises a processor for processing the signals delivered by said series of electrodes, said processor being arranged in the upper part of the outer face of the adhesive seal and said electrodes being distributed on half-circles formed in the lower part of the adhesive seal.

4. The disposable device according to claim 1, wherein the part of the electrodes which is lodged in the adhesive composition has a length which is substantially equal to two thirds of the thickness of the adhesive composition.

5. The disposable device according to claim 1, wherein the adhesive seal further comprises an outer support film which covers the outer face of said seal and on which the detector is mounted, The electrodes passing through said support film and penetrating into the adhesive composition.

6. The disposable device according to one of claims 1, 2, 4, and 5, wherein the adhesive seal comprises a central part covered by the adhesive composition and a ring covered by an adhesive without hydrocolloid surrounding said central part.

7. The disposable device according to one of claims 1, 2, 4, and 5, wherein the alarm comprises a light emitting diode.

8. The disposable device according to one of claims 1, 2, 4, and 5, wherein the alarm comprises an acoustic alarm.

9. The disposable device according to one of claims 1, 2, 4, and 5, wherein the alarm comprises a periodic vibration which can be detected by the patient.

10. The disposable device according to one of claims 1, 2, 4, and 5, wherein the alarm comprises a radio signal which can be received by a remote receiver.

* * * * *